United States Patent [19]

Blaha

[11] Patent Number: 4,767,204

[45] Date of Patent: Aug. 30, 1988

[54] STANDARD SLIT LAMP ADAPTED FOR PHOTOGRAPHIC DOCUMENTATION

[75] Inventor: Erich Blaha, Essingen, Fed. Rep. of Germany

[73] Assignee: Carl-Zeiss-Stiftung, Heidenheim, Fed. Rep. of Germany

[21] Appl. No.: 835,460

[22] Filed: Mar. 3, 1986

[30] Foreign Application Priority Data

Mar. 4, 1985 [DE] Fed. Rep. of Germany ....... 3507571

[51] Int. Cl.$^4$ ............................................... A61B 3/10
[52] U.S. Cl. ..................................... 351/214; 351/221
[58] Field of Search ................ 351/214, 213, 221, 206

[56] References Cited

U.S. PATENT DOCUMENTS 4,461,551  7/1984  Blaha ................................. 351/214
4,504,129  3/1985  Van Iderstine ..................... 351/214

Primary Examiner—Rodney B. Bovernick
Assistant Examiner—P. M. Dzierzynski
Attorney, Agent, or Firm—Walter Ottesen

[57] ABSTRACT

An illuminating unit for a standard slit lamp is described, which can be mounted as a structural unit on the prism head of the standard slit lamp. The illuminating unit enables photographic documentation of the optical sections observed.

9 Claims, 1 Drawing Sheet

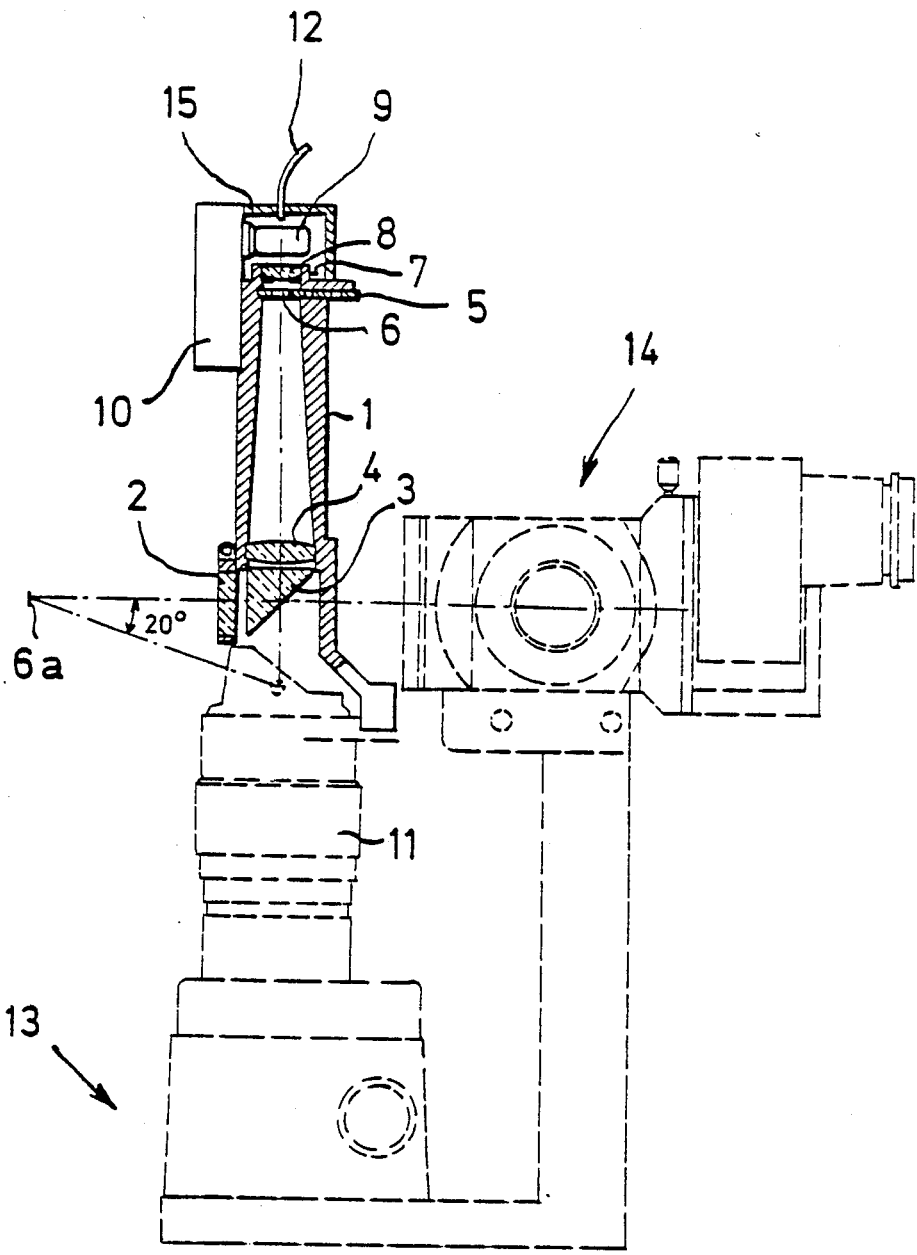

STANDARD SLIT LAMP ADAPTED FOR PHOTOGRAPHIC DOCUMENTATION

FIELD OF THE INVENTION

The invention relates to an illumination unit for photographic documentation with a standard slit lamp.

BACKGROUND OF THE INVENTION

The documentation of eye conditions has great significance in terms of follow-up during a phase of treatment, and it becomes still more important with the increasing use of laser therapy. The areas to be documented include general views of the eye, views in optical section and views of the vitreous body to the retina.

With standard slit lamps, for instance like those described in brochure No. 30-113-d of Carl Zeiss, general views can be taken using a flash unit and a camera apparatus, while for views in optical section and views of the retina, special equipment, preferably photo slit lamps, must be used. With photo slit lamps, a so-called linked illuminating beam path is generally used, where for instance via a double collector system a flash lamp disposed in the intermediate image plane of the double collector system is superimposed on the normal path of the illuminating beam. This arrangement is very expensive in terms of optics, mechanics and energy (high voltage), and the result is that a single-purpose apparatus is required for optical section photography.

This is contrary to the desire of numerous users to be able to perform documentation of the examined area of the eye using a standard slit lamp or a laser slit lamp, without making a major conversion, and without using overly large structural parts that may hinder the course of the examination.

SUMMARY OF THE INVENTION

It is an object of the invention to provide an accessory for slit lamps that enables taking both general photographs of the cornea and photographs in optical section.

This object is attained by using an illumination unit that can be mounted on the lowerable prism head of a standard slit lamp and that includes, in one housing, a photographic light source for illumination, a collector, an iris diaphragm, a slit diaphragm unit having various slit widths, and also a lens and a deflecting prism. The slit diaphragm unit may comprise a Recoss disk, or it may be realized in the form of a continuously adjustable diaphragm.

In an advantageous exemplary embodiment of the invention, a diffusing screen is interchangeably disposed in the direction of the light leading to the patient's eye, before the deflecting prism of the illuminating unit, to enable taking general photographs of the patient's eye.

Using a flash unit as the photographic illumination source is appropriate for the high color temperature required for daylight films at high-intensity illumination. It has proved to be particularly advantageous, however, to use inexpensive flash bulbs such as those used in amateur photography, with either electrical or mechanical triggering. The light source thus becomes very favorable in terms of the minimal electricity it consumes, and it can be used in various forms, either in a serial arrangement or as a single bulb. It is also conceivable to provide an interchangeable arrangement of a number of flash bulbs on a circular ring.

The advantages attained with the invention are above all that the user of a standard slit lamp, by making a small conversion, can convert his equipment into a photographic slit lamp for photographing the optical section, with all the typical characteristics of the standard slit lamp remaining unimpaired.

BRIEF DESCRIPTION OF THE DRAWING

The invention will now be described with reference to the drawing wherein the illumination unit according to the invention is shown in schematic cross section, mounted on a standard slit lamp.

DESCRIPTION OF THE PREFERRED EMBODIMENTS OF THE INVENTION

The single FIGURE of the drawing shows the housing 1 of the illumination unit mounted on the lowerable prism head 11 of a standard slit lamp. Reference numeral 13 indicates the upper part of the slit lamp of this standard slit lamp, and 14 indicates the cornea microscope associated therewith. In the drawing, the prism head 11 has been lowered by the maximum possible amount, so that the axis of its illumination is inclined by 20° from the horizontal. In this position, when the illuminating unit according to the invention is used, the prism head 11 serves to adjust the focusing plane and the area to be photographed. The housing 1 of the illuminating unit can be secured to the prism head 11 by means of a plug-type or screw-type connection. The manner of mounting is not shown in the drawing. The individual elements of the illuminating unit comprise the flash bulb 9, an aspherical collector 8, an iris diaphragm 7 for a variable slit height, a Recoss disk 5 which has various slit widths and corresponding detent positions and is disposed in the slit plane 6, a lens 4 for forming an image of the photographic slit, a deflecting prism 3 and a diffusing screen 2. The plane in which the slit image appears is indicated at 6a.

With the prism head 11 lowered, the illuminating plane of the illuminating unit coincides with the plane of observation of the cornea microscope and hence with that of the camera (not shown). Since the lens 4 forms an image of the slit plane 6 in the plane 6a, it is assured that the photo slit plane and the adjusting slit plane, which is used with the lowered prism head 11 in order to focus the area to be photographed, will coincide. A holder 10 for the flash lamp 9 is attached to the housing 1 and at the same time serves as a housing for the battery for the flash bulbs. The housing 1 is covered at the top by a cap 15. A light conductor 12, into which light from the flash lamp 9 is directed, can be used for illuminating the surrounding field when photographing the optical section.

With the illuminating unit, it is also possible to use an incandescent bulb disposed in the housing, instead of the prism head, for adjusting the focusing plane and the area to be photographed. In this case, the incandescent bulb should be mounted above the flash bulb 9 instead of the cap 15 and should have a double collector system.

It is understood that the foregoing description is that of the preferred embodiments of the invention and that various changes and modifications may be made thereto without departing from the spirit and scope of the invention as defined in the appended claims.

What is claimed is:

1. The combination of a slit lamp having means for photographic documentation and an illumination unit, said combination comprising:

a slit-lamp unit for producing a slit-shaped bundle of rays and having a lowerable prism head; and, the illumination unit including:

a housing defining a light path;

photo-illuminating light source means for generating an illuminating light;

collector means for directing an illuminating beam of light from said light source means down said light path;

an iris diaphragm arranged in said light path;

slit diaphragm means arranged in said light path for defining a plurality of slit widths thereby defining a slit plane;

an objective lens for forming an image of said slit plane in a predetermined plane; and, optical deflecting means for deflecting said image into said predetermined plane; the housing of said illumination unit being mounted to the prism head of said slit lamp.

2. The slit lamp of claim 1, said optical deflecting means being a deflecting prism.

3. The slit lamp of claim 2, comprising a diffusing screen arranged in said light path upstream of said deflecting prism.

4. The slit lamp of claim 3, said diffusing screen being pivotally mounted on said housing for pivoting the same into and out of said light path.

5. The slit lamp of claim 4, said light source means comprising at least one flash lamp.

6. The slit lamp of claim 4, said light source means comprising a flash tube.

7. The slit lamp of claim 4, comprising a light conductor supplied by said light source means and being arranged to illuminate the surrounding field of the subject being photographed.

8. The combination of a slit lamp having means for photographic documentation and illumination means, the combination comprising:

a slit-lamp unit for producing a first slit-shaped bundle of rays during visual examination of an eye and having a first housing including a lowerable prism head;

an illumination unit for producing a second slit-shaped bundle of rays during photographic documentation, said illumination unit having a second housing including flash light source means for providing the illumination needed to effect said photographic documentation;

said second housing being mounted on top of said prism head; and, said illumination unit further including:

collector means for directing an illuminating beam of light from said flash light source means along a light path;

an iris diaphragm arranged in said light path;

slit diaphragm means arranged in said light path for defining a plurality of slit widths thereby defining a slit plane;

an objective lens for forming an image of said slit plane in a predetermined plane; and, a diffusing screen mounted to said second housing for switching the same in and out of said light path.

9. An ancillary illuminating device for a slit lamp having means for photographic documentation, the slit lamp producing a first slit-shaped bundle of rays during visual examination of an eye, said slit lamp including an elongated first housing defining a longitudinal axis and a lowerable prism head mounted on the top of said first housing; the ancillary illuminating device comprising:

an illumination unit for producing a second slit-shaped bundle of rays during photographic documentation, said illumination unit having a second housing and lens means mounted in said housing for conducting said second bundle of rays along an optical axis;

seating means provided on said prism head for accommodating said second housing thereon so as to cause said axes to be coincident; and, said illumination unit including light source means for the illumination needed to effect said photographic documentation.

* * * * *